US00PP33755P2

(12) United States Plant Patent
NeSmith

(10) Patent No.: US PP33,755 P2
(45) Date of Patent: Dec. 21, 2021

(54) SOUTHERN HIGHBUSH BLUEBERRY PLANT NAMED 'TH-1493'

(50) Latin Name: *Vaccinium corymbosum*
Varietal Denomination: TH-1493

(71) Applicant: University of Georgia Research Foundation, Inc., Athens, GA (US)

(72) Inventor: D. Scott NeSmith, Griffin, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/174,872

(22) Filed: Feb. 12, 2021

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./156, 157
See application file for complete search history.

*Primary Examiner* — Susan McCormick Ewoldt
*Assistant Examiner* — Karen M Redden
(74) *Attorney, Agent, or Firm* — Thomas Horstemeyer, LLP

(57) ABSTRACT

A new and distinct cultivar of *Vaccinium* plant named 'TH-1493', characterized by a combination of early season flowering and ripening, large berries with good color and flavor, high quality fruit production in conventional production areas, and a chilling requirement of about 350-450 hours below about 45° F.

6 Drawing Sheets

Botanical designation: *Vaccinium corymbosum.*
Cultivar denomination: 'TH-1493'.

BACKGROUND OF THE INVENTION

The present invention relates to a new and distinct cultivar of southern highbush blueberry plant, botanically know as *Vaccinium corymbosum*, and hereinafter referred to by the cultivar name 'TH-1493'.

The new *Vaccinium corymbosum* 'TH-1493' was first identified in 2012 in Griffin, Ga. The new variety 'TH-1493' is early season, has large berries with good color and flavor, with no observed notable diseases or other pest problems beyond those also common for other varieties, and a chilling requirement of about 350-450 hours below about 45° F.

'TH-1493' is a product of a cross of 'TH-909' X 'TH-681' made by D. Scott NeSmith in 2009. Both 'TH-909' and 'TH-681' are not patented. The new blueberry plant variety 'TH-1493' has been tested in asexually propagated (by vegetative cuttings) plantings in Alapaha, Ga. since 2013 where it was established for testing and comparing to industry standards. Observations of the resulting 'TH-1493' progeny have shown that the unique features of this new *Vaccinium corymbosum* 'TH-1493' are stable and reproduced true to type in successive generations.

SUMMARY OF THE INVENTION

The new *Vaccinium* cultivar 'TH-1493' has not been observed under all possible environmental conditions. The phenotype may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Vaccinium corymbosum* cultivar named 'TH-1493'. In combination, these traits set 'TH-1493' apart from all other existing varieties of southern highbush blueberry known to the inventors.

1. early flowering and ripening
2. large fruit with good color and flavor
3. no significant diseases or pests not also common to other southern highbush varieties.
4. high quality fruit production in conventional production areas Comparison: As compared to the female parent 'TH-909' and male parent 'TH-681', plants of the new *Vaccinium* cultivar 'TH-1493' have a chilling requirement of about 350-450 hours, which is lower than 'TH-681' (450 to 550 hours) but higher than 'TH-909' (200 to 300 hours). The flowering time for 'TH-1493' (March 2 on average) is before 'TH-681' (March 7 to March 14 on average), but after 'TH-909' (February 21 to February 28 on average). Ripening time of 'TH-1493' (May 9 on average) is before 'TH-681' (May 12 to May 18 on average), and later than 'TH-909' (May 1 to May 7 on average). Berry color for 'TH-1493' averages 8.0/10, whereas 'TH-681' averages 8.5/10 and 'TH-909' averages 7.0/10. Berry firmness of 'TH-1493' averages 7.5/10, whereas 'TH-681' averages 6.5/10 and 'TH-909' averages 7.8/10. Berry size of 'TH-1493' averages 8.5/10, whereas 'TH-681' averages 8.8/10 and 'TH-909' averages 7.5/10.

Plants of the new *Vaccinium corymbosum* can also be compared to other early season southern highbush blueberry cultivars 'Suziblue' (U.S. Plant Pat. No. 21,167) and 'Rebel' (U.S. Plant Pat. No. 18,138). The selection 'TH-1493' begins flowering and ripening slightly later than 'Suziblue' and 'Rebel' in South Georgia and has a similar flowering and harvest period. 'TH-1493' has large berries with good color and flavor as compared to 'Suziblue' and 'Rebel' at Alapaha (Table 1). No notable diseases or other pest problems have been observed for the new variety that are not also common for other varieties. The new variety is estimated to have a chilling requirement of 350 to 450 hours, more or less, below 45° F. (based on comparison of flowering dates with those of known standard cultivars) when produced under typical low to mid chill production regions. Studies suggest that 'TH-1493' produces high quality fruit when grown in conventional production areas. Additional comparison data of 'TH-1493' with 'Suziblue' and 'Rebel' are presented in the table below.

TABLE 1

Plant and fruit ratings for 'TH-1493' and standards grown in Alapaha, GA. Data represents and average of data from 3 years (2016, 2019, and 2020).

| | 'Suziblue' | 'Rebel' | 'TH-1493' |
|---|---|---|---|
| Berry size | 8.0 | 7.6 | 8.5 |
| Berry scar | 7.0 | 7.2 | 7.1 |
| Berry color | 7.0 | 7.0 | 8.0 |
| Berry firmness | 7.3 | 7.2 | 7.5 |
| Berry flavor | 7.0 | 6.3 | 7.5 |
| Cropping | 8.5 | 7.0 | 6.5 |
| Plant vigor | 8.0 | 8.2 | 7.8 |
| Date of 50% flowering | Feb. 28 | Feb. 26 | Mar. 2 |
| Date of 50% ripening | May 7 | Apr. 27 | May 9 |
| Fruit development period (days) | 69 | 61 | 68 |

BRIEF DESCRIPTION OF THE DRAWINGS

The accompanying colored photographic illustrations show the overall appearance and distinct characteristics of the new cultivar of *Vaccinium corymbosum* 'TH-1493' showing the colors as true as possible. Colors in the photographs may differ slightly from the color values cited in the detailed botanical description, which accurately describes the colors of the new *Vaccinium corymbosum* 'TH-1493'. The photographs were taken of plants grown outdoors in Alapaha, Ga. taken in 2016.

The photograph labeled

The photograph labeled

The photograph labeled

The photograph labeled

The photographs labeled

The photograph labeled

DETAILED BOTANICAL DESCRIPTION

Figure 1:
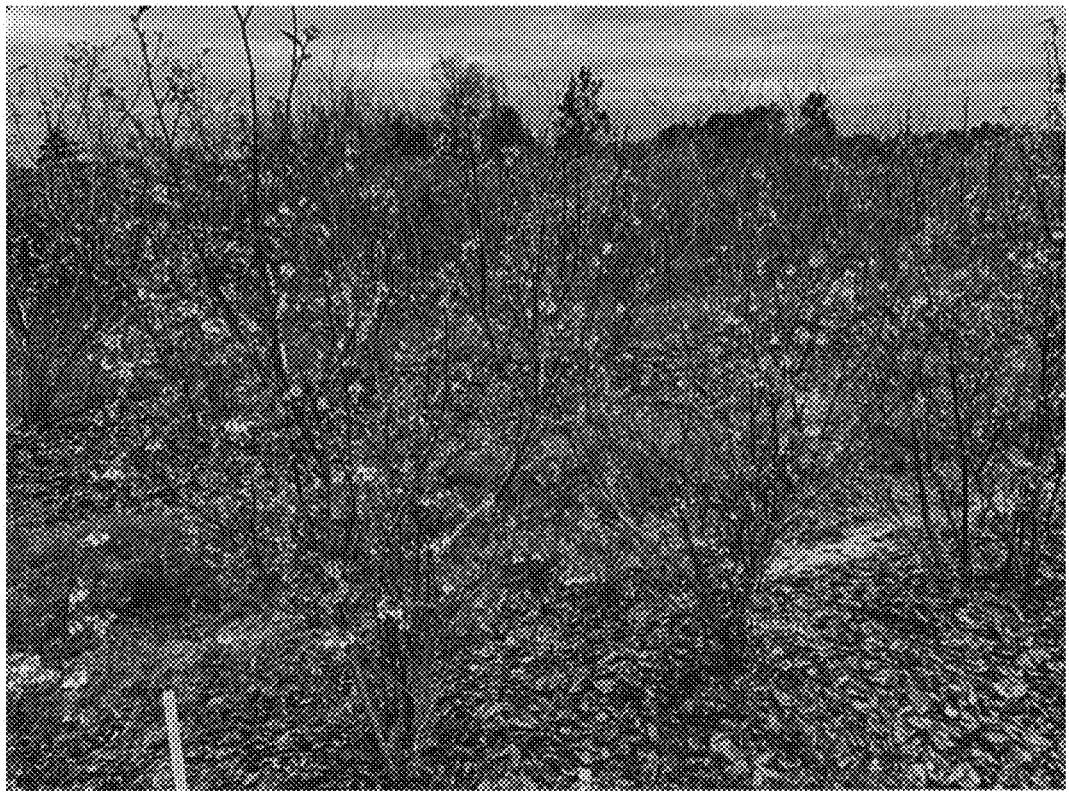
FIG. 1 depicts typical three-year old 'TH-1493' plants during flowering, taken in March 2016.
Figure 2:
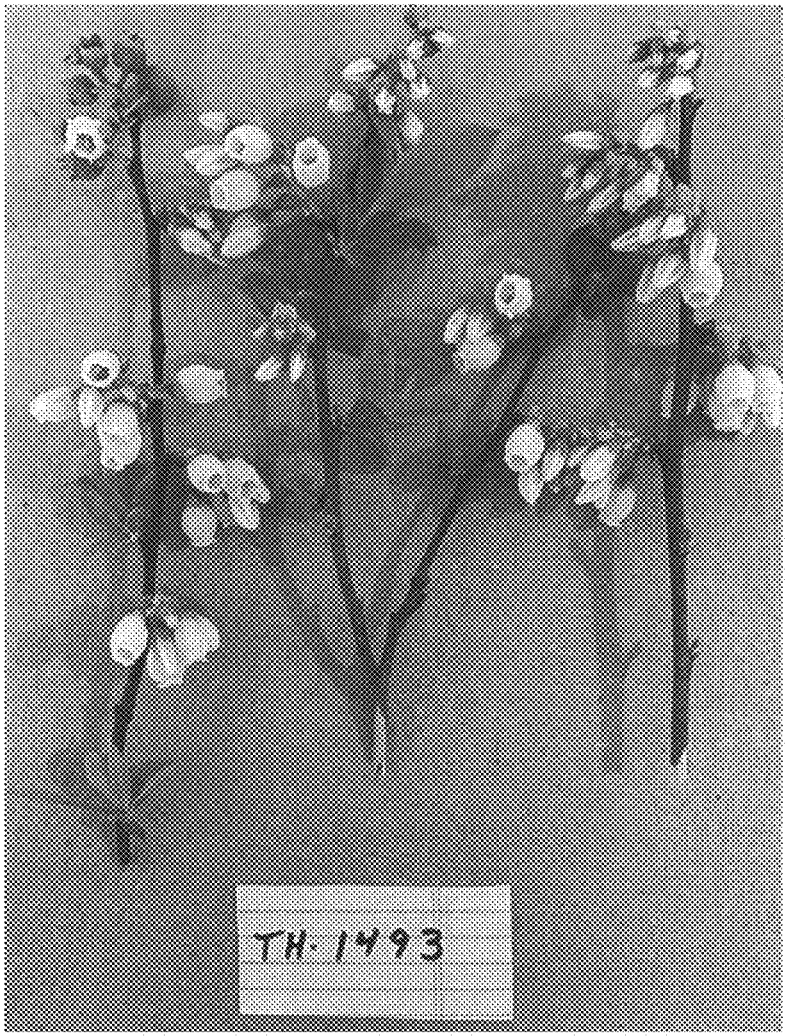
FIG. 2 depicts a close-up view of a flowering branch of a 'TH-1493' plant.
Figure 3:
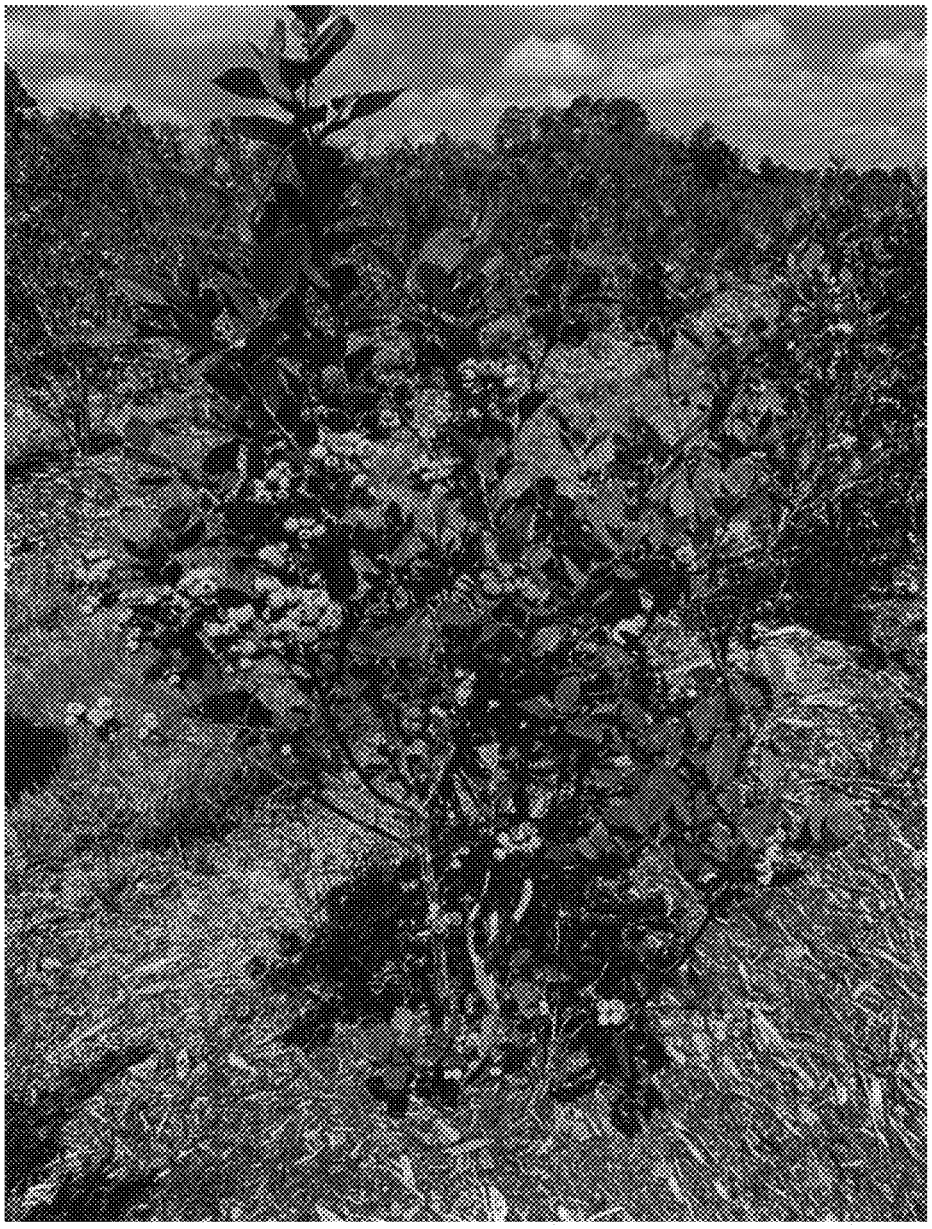
FIG. 3 depicts typical three-year old plants of 'TH-1493' during fruit ripening, taken in May 2016.
Figure 4:
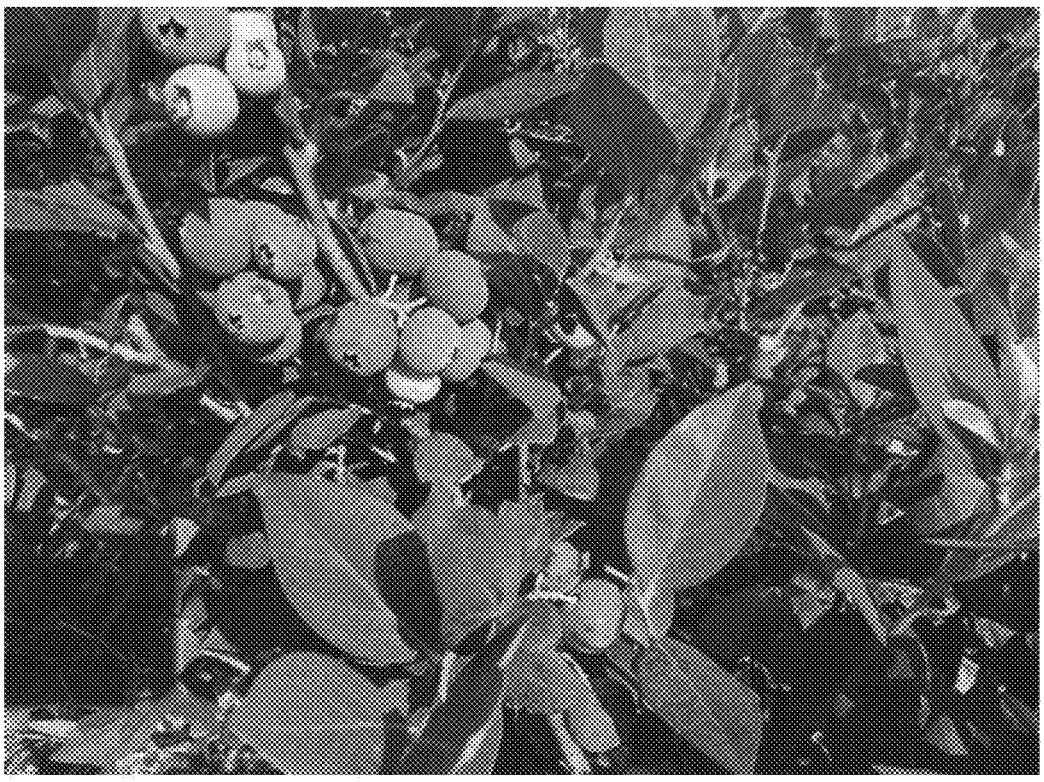
FIG. 4 depicts close-up view of maturing fruit of 'TH-1493', taken in May 2016.
Figure 5A:
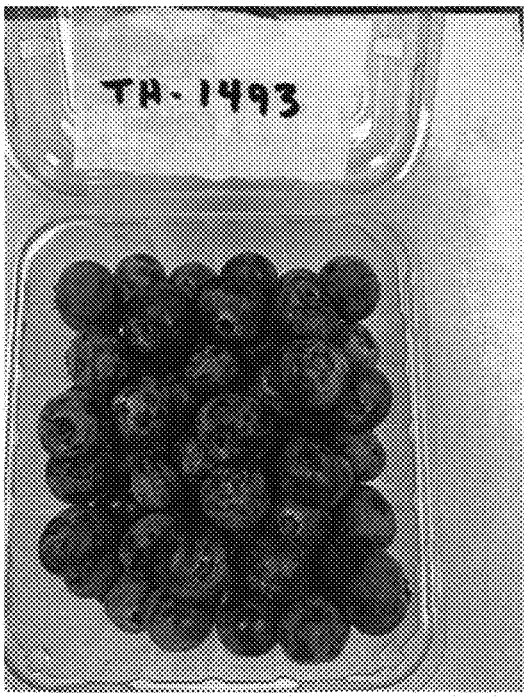
FIG. 5A and FIG. 5B are close-up views of ripe fruit of 'TH-1493', with FIG. 5B depicting two sliced berries to reveal the inside of the fruit.
Figure 5B:
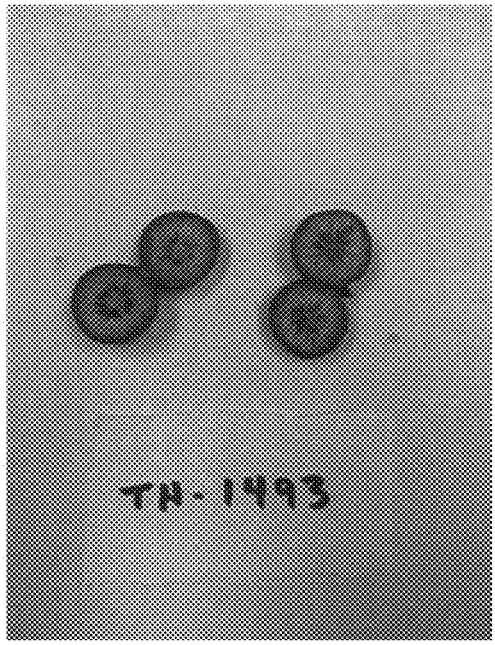
Figure 6:
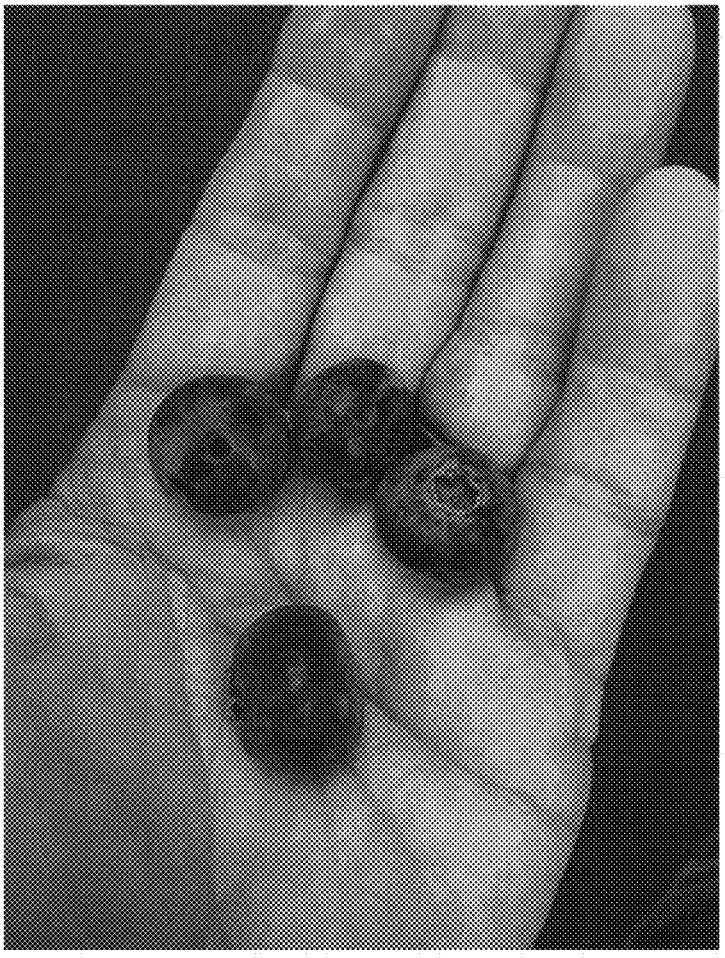
FIG. 6 is another close-up view of ripe fruit of 'TH-1493', in a human hand, illustrating the relative size of the fruit.

The following traits have been consistently observed in the original plant of this new variety and in asexually propagated progeny grown in Alapaha, Ga., and, to the best knowledge of the inventors, their combination forms the unique characteristics of the new variety *Vaccinium corymbosum* 'TH-1493'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England in 2007, except where general terms of ordinary dictionary significance are used.

The aforementioned photographs and following observations, measurements, and values describe plants of the *Vaccinium corymbosum* cultivar named 'TH-1493'. Data were collected between the years of 2015-2017 from a horticulture farm and nursery in Alapaha, Ga. from 2 to 4-year-old plants (planted in the field with supplemental irrigation). The average low temperature for the year ranges from about 54° F. to 58° F., and the average high temperature for the year ranges from about 78° F. to 82° F.

Botanical classification: *Vaccinium corymbosum* 'TH-1493'.

*Commercial classification.*—Fruit-bearing shrub.

*Parentage.*—'TH-909' X 'TH-681'.

Growth and propagation:

*Propagation type.*—Vegetative by softwood cuttings.

*Growth rate.*—Moderately vigorous.

*Root description.*—Fibrous.

Plant description:

*Growth habit.*—Plant is strongly upright, with about 1 to 3 main canes arising from the original crown, and multiple branching of shoots from those canes about 15 to 25 cm above ground.

*Usage.*—Commercial and private fruit production.

*Productivity.*—Medium to high yielding. Yields of about 5 to 8 lbs fruit per plant each year on plants 4 years old or older grown under well fertilized and irrigated field conditions. Frost protection may be useful to reach yield potential in some years.

*Size of plant.*—Plant is about 1.3 to 1.6 m tall by 3 to 4 years. Plants grown under highly productive soil and fertility conditions may exceed about 1.6 m tall in 4 years. The plant crown, or base, is very narrow, typically about 10-15 cm in diameter. Upper portion of plant canopy reaches about 1.0 to 1.3 m in diameter by 3 to 4 years.

*Cold hardiness.*—Similar to other early ripening southern highbush varieties.

*Disease resistance.*—No notable disease resistance or susceptibility observed. Estimated to be similar to other early season southern highbush such as 'Suziblue' and 'Rebel'.

*Chilling requirement.*—Plants are medium chill, requiring only about 350 to 450 hours of temperatures at or below 45 F. (7 C.) to induce normal leafing and flowering during the spring under conventional dormant production systems. The chill requirement is more than the female parent 'TH-909' (non-patented breeding selection; 200 to 300 hours of chilling required) and less than the male parent 'TH-681' (non-patented breeding selection, 450 to 500 hours of chilling required).

*Leafing.*—Plants tend to break sufficient leaf buds simultaneously with, or shortly after, anthesis.

*Canes.*—Main cane base diameter about 20 to 30 mm, color most near Brown N 200C to Grey 201C; two year-old cane diameter 10 to 15 mm, color transitioning from Greyed Orange 166C to Grey 201C; one-year-old wood diameter about 5 to 10 mm, color Yellow Green 145C.

*Fruiting wood*.—Moderate number of twigs (about 5 to 8 common) of about 15 to 25 cm in length, with internode lengths of about 15 to 25 mm common.

Foliage:

*Leaf color*.—Healthy mature leaves: top side of leaf color is Green 137B, under side of leaf color is Green 138C.

*Leaf arrangement*.—Alternate, simple.

*Leaf shape*.—Elliptic.

*Leaf margins*.—Slightly to moderately crenate; older leaves become mostly entire.

*Leaf venation*.—Pinnate with slight netting.

*Leaf apices*.—Acute.

*Leaf bases*.—Acute.

*Leaf dimensions*.—Length: about 60 to 70 mm; width: about 30 to 35 mm.

*Petioles*.—Small, about 5.0 to 7.0 mm long, about 1.5 to 2.0 mm wide; Color: Yellow Green 145C.

*Texture*.—Both upper and lower leaf surfaces glaucous.

Flowers:

*Date of* 50% *anthesis*.—3-year average March 2 in southeast Georgia.

*Flower shape*.—Urceolate.

*Flower bud number*.—High to very high, averaging 3 to 6 buds per fruiting shoot.

*Flowers per cluster*.—4 to 8 common.

*Flower fragrance*.—Slight to moderate cut flower/rose fragrance.

*Corolla color*.—White NN 155B to NN 155C.

*Corolla length*.—9.5 to 10.5 mm.

*Corolla width*.—8.0 to 9.0 mm.

*Corolla aperture width*.—3.0 to 4.0 mm.

*Flower peduncle*.—Length 15.0 to 25.0 mm; Color: Yellow Green 145C.

*Flower pedicel*.—Length 5.0 to 8.0 mm; Color: Green 138D.

*Calyx* (*with sepals*).—Diameter: 6.5 to 7.5 mm; Color: sepals Green 138C; calyx center Green 138B.

*Stamen*.—Length: 8.0 to 9.0 mm; number per flower: 10; filament color: Green White 157C to 157D.

*Style*.—Length: 9.5 to 10.5 mm; Color: Yellow Green 145B.

*Pistil*.—Length: 11.5 to 12.5 mm; ovary color: Green 138C.

*Anther*.—Length: 4.0 to 5.0 mm; number: 10; Color: Greyed Orange 164B.

*Pollen*.—Abundance: medium; Color: White NN 155A.

*Compatibility*.—The cultivar has a moderate degree of self-compatibility.

Fruit:

*Date of* 50% *maturity*.—3-year average May 9 in southeast Georgia.

*Fruit development period*.—About 68 days in southeast Georgia.

*Berry color*.—With wax Violet Blue 97B to Blue 100D; with wax removed Black 203C.

*Berry flesh color*.—Green White 157C.

*Berry surface wax abundance*.—Medium to high.

*Berry weight*.—$1^{st}$ harvest: about 3.7 to 4.5 g; $2^{nd}$ harvest: about 2.8 to 3.4 g.

*Berry size*.—Height from calyx to scar: about 17 to 19 mm; diameter: about 18 to 22 mm.

*Berry shape*.—Semi-spherical to spherical.

*Fruit stem scar*.—Small to medium, dry, with no tearing upon harvest.

*Calyx*.—Depth medium, about 2.0 to 3.0 mm; width medium, about 5.0 to 7.0 mm; sepals nearly absent, flat or inwards when present, <about 1 mm.

*Berry firmness*.—Good.

*Berry flavor and texture*.—Good sweetness, mildly acid flavor; very smooth texture.

*Storage quality*.—Good.

*Suitability for mechanical harvesting*.—Not likely suitable.

*Uses*.—Primarily to be used as fresh fruit for shipping and processing markets.

Seed:

*Seed abundance in fruit*.—Medium, about 10 to 20 fully developed seeds per berry.

*Seed color*.—Greyed Orange 165B.

*Seed dry weight*.—33.8 mg per 100 seed.

*Seed size*.—About 1.2 to 1.7 mm long.

It is claimed:

1. A new and distinct cultivar of the *Vaccinium* plant named 'TH-1493' as illustrated and described herein.

* * * * *